(12) United States Patent
Wu et al.

(10) Patent No.: US 10,966,595 B2
(45) Date of Patent: Apr. 6, 2021

(54) ENDOSCOPY AUXILIARY DEVICE

(71) Applicant: INSIGHT MEDICAL SOLUTIONS INC., Hsinchu (TW)

(72) Inventors: Yu-Jen Wu, Taichung (TW);
Ching-Lung Kuo, Hsinchu (TW);
Chih-Hao Chang, Taichung (TW);
Ping-Chun Tsai, Hsinchu (TW);
Shih-Chieh Lu, Hsinchu (TW)

(73) Assignee: INSIGHT MEDICAL SOLUTIONS INC., Hsinchu (TW)

( * ) Notice: Subject to any disclaimer, the term of this patent is extended or adjusted under 35 U.S.C. 154(b) by 873 days.

(21) Appl. No.: 15/613,126

(22) Filed: Jun. 2, 2017

(65) Prior Publication Data
US 2017/0347864 A1 Dec. 7, 2017

(30) Foreign Application Priority Data
Jun. 3, 2016 (TW) .................... 105117685

(51) Int. Cl.
*A61B 1/00* (2006.01)
*A61B 5/00* (2006.01)
(Continued)

(52) U.S. Cl.
CPC ........ *A61B 1/00154* (2013.01); *A61B 1/0014* (2013.01); *A61B 1/00128* (2013.01);
(Continued)

(58) Field of Classification Search
CPC . A61B 1/00089; A61B 1/041; A61B 1/00147; A61B 1/00154; A61B 1/0008;
(Continued)

(56) References Cited

U.S. PATENT DOCUMENTS 3,757,781 A * 9/1973 Smart ............... A61M 37/0069
604/59
3,934,584 A * 1/1976 Corio ....................... A61D 7/00
604/59
(Continued)

FOREIGN PATENT DOCUMENTS

CN 1140235 C 3/2004
CN 102448364 A 5/2012
(Continued)

OTHER PUBLICATIONS

CN Office Action in application No. 201710333267.6 dated Aug. 28, 2018.

*Primary Examiner* — Ryan N Henderson
(74) *Attorney, Agent, or Firm* — Maschoff Brennan (57) ABSTRACT

An endoscopy auxiliary device includes an insertion tube and a clamping unit. The clamping unit has a pipe and a connector. The connector is connected to the insertion tube. The tube is configured to clamp a capsule endoscope. The pipe has an inner space configured to accommodate a part of the capsule endoscope. The pipe includes a first slit, a second slit and a third slit. The first slit extends from a free end of the pipe for a first distance toward a connection end of the pipe. The second slit extends from the free end of the pipe for the connection distance toward the connection end of the pipe. The third slit extends from the free end of the pipe for a third distance toward the connection end of the pipe. The first slit, the second slit and the third slit are separate.

14 Claims, 11 Drawing Sheets

(51) Int. Cl.
*A61B 1/04* (2006.01)
*A61B 5/07* (2006.01)

(52) U.S. Cl.
CPC ...... *A61B 1/00131* (2013.01); *A61B 1/00147* (2013.01); *A61B 1/041* (2013.01); *A61B 5/6861* (2013.01); *A61B 5/0084* (2013.01); *A61B 5/073* (2013.01); *A61B 5/6852* (2013.01); *A61B 2560/063* (2013.01)

(58) Field of Classification Search
CPC ............ A61B 1/00101; A61B 1/00131; A61B 1/0014; A61B 1/273; A61B 1/2733; A61B 1/2736; A61B 1/31; A61B 1/313; A61B 1/3132; A61B 5/6861
See application file for complete search history.

(56) References Cited

U.S. PATENT DOCUMENTS

| | | | |
|---|---|---|---|
| 5,604,531 A | 2/1997 | Iddan et al. | |
| 5,653,677 A * | 8/1997 | Okada | A61B 1/00016 600/112 |
| 5,913,865 A * | 6/1999 | Fortier | A61B 17/12013 606/140 |
| 6,432,075 B1 * | 8/2002 | Wada | A61F 13/26 604/15 |
| 6,676,672 B2 * | 1/2004 | Chu | A61B 17/12013 606/139 |
| 10,219,882 B1 * | 3/2019 | Cohen, Jr. | A61D 7/00 |
| 2001/0051766 A1 * | 12/2001 | Gazdzinski | A61B 1/00156 600/309 |
| 2003/0013938 A1 * | 1/2003 | Iddan | A61B 1/041 600/129 |
| 2003/0120130 A1 * | 6/2003 | Glukhovsky | A61B 1/00183 600/109 |
| 2003/0139647 A1 * | 7/2003 | Raz | A61M 31/007 600/104 |
| 2005/0267361 A1 | 12/2005 | Younker et al. | |
| 2007/0049796 A1 * | 3/2007 | Fujikura | A61B 1/00089 600/116 |
| 2007/0225552 A1 * | 9/2007 | Segawa | A61B 1/041 600/102 |
| 2008/0015413 A1 * | 1/2008 | Barlow | A61B 1/273 600/114 |
| 2009/0076325 A1 * | 3/2009 | Yokoi | A61B 1/041 600/118 |
| 2010/0081877 A1 * | 4/2010 | Vakharia | A61B 1/00135 600/121 |
| 2011/0282144 A1 * | 11/2011 | Gettman | A61B 1/041 600/109 |
| 2012/0101331 A1 | 4/2012 | Gilad et al. | |
| 2014/0194736 A1 * | 7/2014 | Tearney | A61B 5/0059 600/425 |
| 2014/0243598 A1 * | 8/2014 | Genier | A61B 1/00147 600/114 |
| 2015/0230695 A1 | 8/2015 | Hong et al. | |

FOREIGN PATENT DOCUMENTS

| | | |
|---|---|---|
| CN | 103156568 A | 6/2013 |
| TW | 200940024 A | 10/2009 |
| TW | 201532588 A | 9/2015 |
| WO | 99/32028 A2 | 7/1999 |

* cited by examiner

ENDOSCOPY AUXILIARY DEVICE

CROSS-REFERENCE TO RELATED APPLICATIONS

This non-provisional application claims priority under 35 U.S.C. § 119(a) on Patent Application No(s). 1105117685 filed in Taiwan, R.O.C. on Jun. 3, 2016, the entire contents of which are hereby incorporated by reference.

TECHNICAL FIELD

The disclosure relates to an endoscopy auxiliary device, more particularly to an endoscopy auxiliary device for a capsule endoscope.

BACKGROUND

In general, for the purpose of examining whether lesions exist inside patients' bodies (e.g. esophagus, stomachs or intestines), doctors would place capsule endoscopies into patients' bodies so that the conditions inside the patients' bodies can be observed by the images captured through camera lens of the capsule endoscopies. Traditionally, tube endoscopies can be used for directly being pushed into digestive tracts for examining the lesions. Recently, due to the invention of capsule endoscopies, the capsule endoscopies can be used for being swallowed to get into patients' bodies, and then the patients' digestive tracts can be examined through image data transmission implemented by radio waves, such as contents disclosed in the U.S. patent (U.S. Pat. No. 5,604,531). So far, the capsule endoscopies can not be utilized in large organs such as stomachs due to limitations of power and wireless transmission techniques.

Recently some inventors control capsule endoscopies by using magnetic force. For example, as disclosed in the Taiwanese patent (publication No. 10310549), the purpose of examining stomachs is achieved through swallows of patients for the capsule endoscopies. Although capsule endoscopies are small, patients still feel uncomfortable as swallowing the capsule endoscopies because of wires of the capsule endoscopies, so that difficulties of swallowing are caused and then processes of examinations are interfered. European patent (WO 99/32028) discloses a device for delivering capsule endoscopies. In this device, the capsule endoscope is clamped using a clamper so that is can be placed into patients' bodies. However, an extra manual pull is required to manipulate the clamper so that the capsule endoscope can be removed away from the clamper and then left in patients' bodies.

SUMMARY

According to one embodiment of the present disclosure, an endoscopy auxiliary device is disclosed. The auxiliary device includes an insertion tube and a clamper. The clamper has a pipe and a connector. The connector is connected to the insertion tube. The pipe is configured to clamp a capsule endoscope. The pipe has an inner space configured to accommodate part of the capsule endoscope. The pipe includes a first slit, a second slit and a third slit. The first slit extends from a free end of the pipe for a first distance toward a connection end of the pipe. The second slit extends from the free end of the pipe for a second distance toward the connection end of the pipe. The third slit extends from the free end of the pipe for the third distance toward the connection end of the pipe. Wherein the first slit, the second slit and the third slit are separated from each other, and the first distance is greater than the second distance and the third distance.

According to one embodiment of the present disclosure, in the auxiliary device, the pipe has a body. The body has a chamber, and the chamber is communicated with the inner space.

According to one embodiment of the present disclosure, the auxiliary device further includes an electromagnet disposed in the connector and configured to selectively generate a magnetic force according to an external current for selectively attracting the capsule endoscope.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
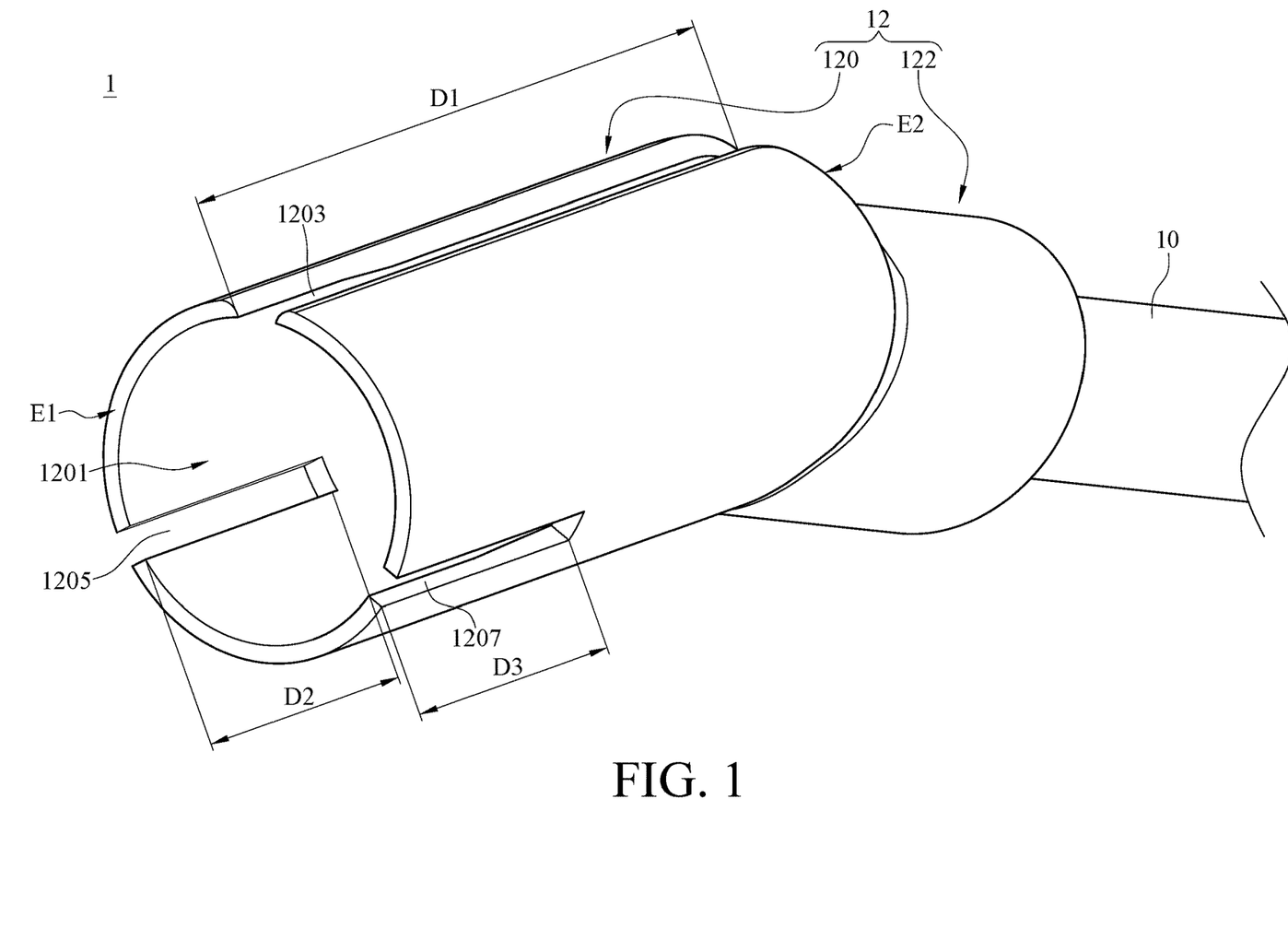
FIG. 1 is a schematic diagram of an endoscopy auxiliary device according to one embodiment of the present disclosure.

Please refer to FIG. 1, which is a schematic diagram of an endoscopy auxiliary device according to one embodiment of the present disclosure. As shown in FIG. 1, the endoscopy auxiliary device 1 includes an insertion tube 10 and a clamper 12. The clamper 12 has a pipe 120 and a connector 122. The connector 122 is connected to the insertion tube 10. The pipe 120 is configured to clamp a capsule endoscope (not shown in FIG. 1). The pipe 120 has an inner space 1201 configured to accommodate part of the capsule endoscope.

Specifically, the capsule endoscope is placed into the space 1201 of the clamper 12 so that part of the capsule endoscope can be clamped by the clamper 12. Thereby, the capsule endoscope does not fall off easily during the process that the capsule endoscope is placed in the patients' bodies by pushing the auxiliary device. In one embodiment, a condition of vacuum is formed between the capsule endoscope and the edge of the inner space 1201, and the condition of vacuum means a physical phenomenon that the air pressure in the area between the edge of the inner space 1201 and the capsule endoscope is far less than the atmospheric pressure. The capsule endoscope can be absorbed within the inner space 1201 through the condition of vacuum. Thereby, the capsule endoscope would not fall off easily during the process that doctors put the auxiliary device carrying the capsule endoscope into patients' bodies. In one embodiment, the clamper 12 is elastic, and the pipe 120 is integrally connected to the connector 122. In another embodiment, the pipe 120 is not integrally connected to the connector 122. Instead, the pipe 120 and the connector 122 are components independent of each other.

The pipe 120 includes a first slit 1203, a second slit 1205 and a third slit 1207. The first slit 1203 extends from the free end E1 of the pipe 120 for a first distance D1 toward the connection end E2 of the pipe 120. The second slit 1205 extends from the free end E1 of the pipe 120 for a second distance D2 toward the connection end E2 of the pipe 120. The third slit 1207 extends from the free end E1 of the pipe 120 for a third distance D3 toward the connection end E2 of the pipe 120. The first slit 1203, the second slit 1205 and the third slit 1207 are separated from each other. In one embodiment, the first slit 1203, the second slit 1205 and the third slit 1207 are separated from each other in an equal distance, which means the first slit 1203, the second slit 1205 and the third slit 1207 are disposed equally on a circumference so that the distances between any two of the first slit 1203, the second slit 1205 and the third slit 1207 are the same.

In another embodiment, the distances between any two of the first slit 1203, the second slit 1205 and the third slit 1207 are not the same. For example, the location where the first slit 1203 is disposed is close to the location where the second slit 1205 is disposed. Both the location where the first slit 1203 is disposed and the location where the second slit 1205 is disposed are far away from the location where the third slit 1207 is disposed. The first distance D1 of the first slit 1203 is greater than the second distance D2 of the second slit 1205 and the third distance D3 of the third slit 1207. In one embodiment, both the second distance D2 and the third distance D3 are not greater than half of the first distance D1, so the capsule endoscope can be clamped more tightly. Thereby, the situation that the capsule endoscope falls off due to the oversize second distance D2 and the oversize third distance D3 can be avoided. In another embodiment, both the second distance D2 and the third distance D3 are one third of the first distance D1. Thereby, the capsule endoscope is not only clamped tightly in the process that the endoscope auxiliary device 1 is put into the patient's body, but also easily dropped off in the process that the endoscopy auxiliary device 1 is pulled out of the patient's body.

Figure 2:
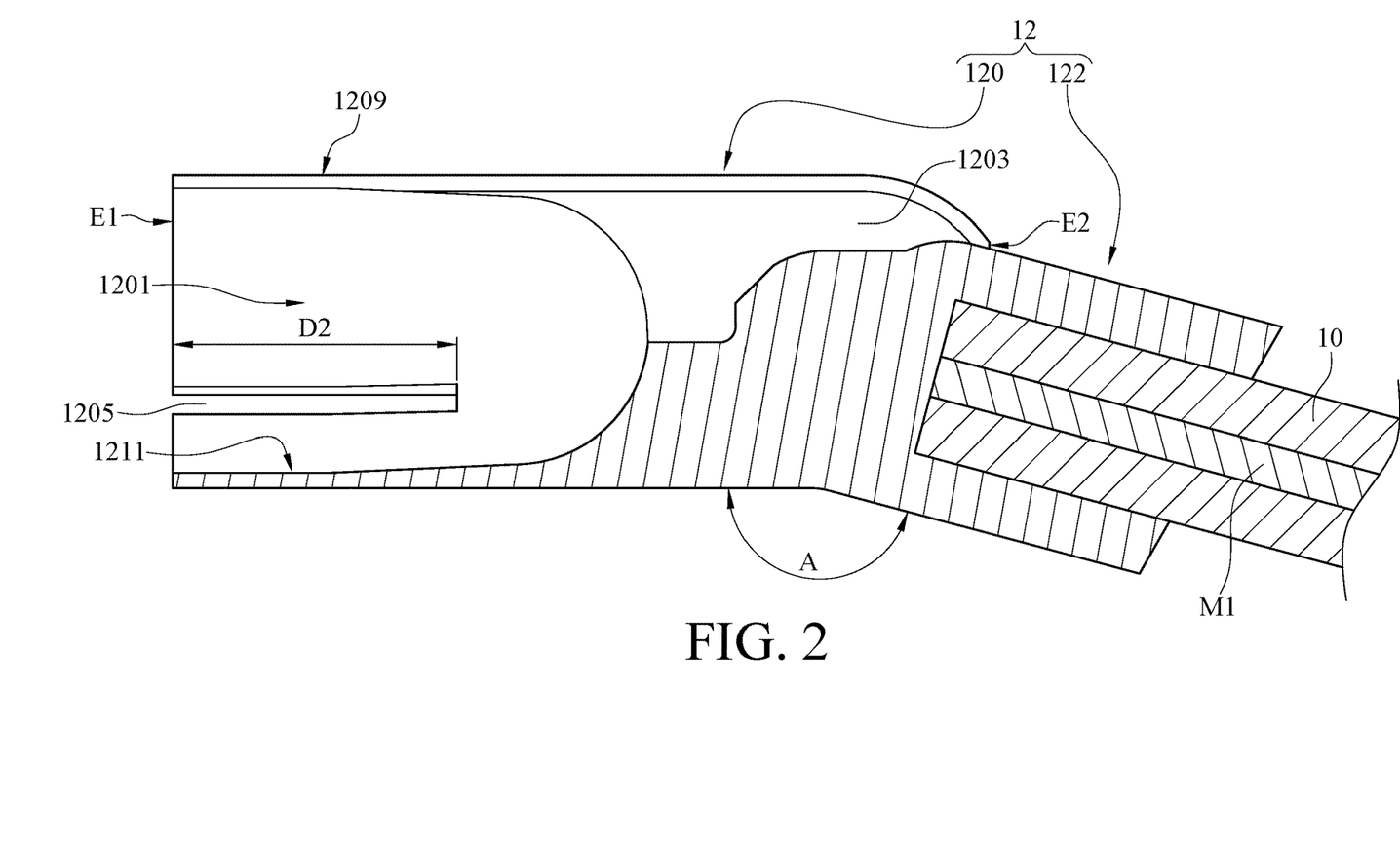
FIG. 2 is a sectional diagram of the endoscopy auxiliary device according to one embodiment of the present disclosure.

Please refer to FIG. 1 and FIG. 2. FIG. 2 is a sectional diagram of the endoscopy auxiliary device according to one embodiment of the present disclosure. As shown in FIG. 2, the first slit 1203 extends from the free end E1 of the pipe 120 to the connection end E2 of the pipe 120. The pipe 120 has an inner surface 1211 and an outer surface 1209. An extending distance of the first slit 1203 along the inner surface 1211 is less than an extending distance of the first slit 1203 along the outer surface 1209. Therefore, when the capsule endoscope disposed in the clamper 12 carries a wire, the first slit 1203 can be used for accommodating the wire of the capsule endoscope, so that the wire of the capsule endoscope in the clamper 12 can be smoothly connected to external computers or other displays receiving image data. Thereby, the capsule endoscope carrying the wire can be clamped tightly by the clamper 12, and the capsule endoscope carrying the wire would not be dropped from the inner space 1201 by the wire bended. Moreover, through the first slit 1203, damages of wire extrusion can be avoided so that negative effects on data transmission can be reduced. It is noted that the present disclosure is not limited to applications of a capsule endoscope carry a wire. In other embodiment, the present disclosure can be applied to a wireless capsule endoscope.

In practice, the insertion tube 10 consists of materials having features of flexibility and softness, such as silicones, rubbers or plastics. In one embodiment, as shown in FIG. 2, at least one flexible metal wire M1 is disposed inside the insertion tube 10. The at least one flexible metal wire M1 is used for supporting the insertion tube 10. For example, the insertion tube 10 is a multi-center structure, and one or more metal wires are disposed within the insertion tube 10. Since the insertion tube 10 consists of materials having features of flexibility and softness, the doctor is allowed to adjust the shape of the insertion tube 10 using the one or more flexible metal wire according to actual demands. For example, according to actual demands, the shape of the insertion tube 10 can be adjusted through changing the shape of flexible metal wires to achieve a better operation. In one embodiment, the endoscopy auxiliary device 1 further has a handle (not shown in FIG. 1) connected to another end of the insertion tube 10 (opposite to the end of the insertion tube 10 connected to the clamper 12). The handle is used for raising the convenience of holding the endoscopy auxiliary device 1. The handle is equipped with a button. By pressing the button, the handle and the insertion tube 10 can be separated rapidly.

Figure 3:
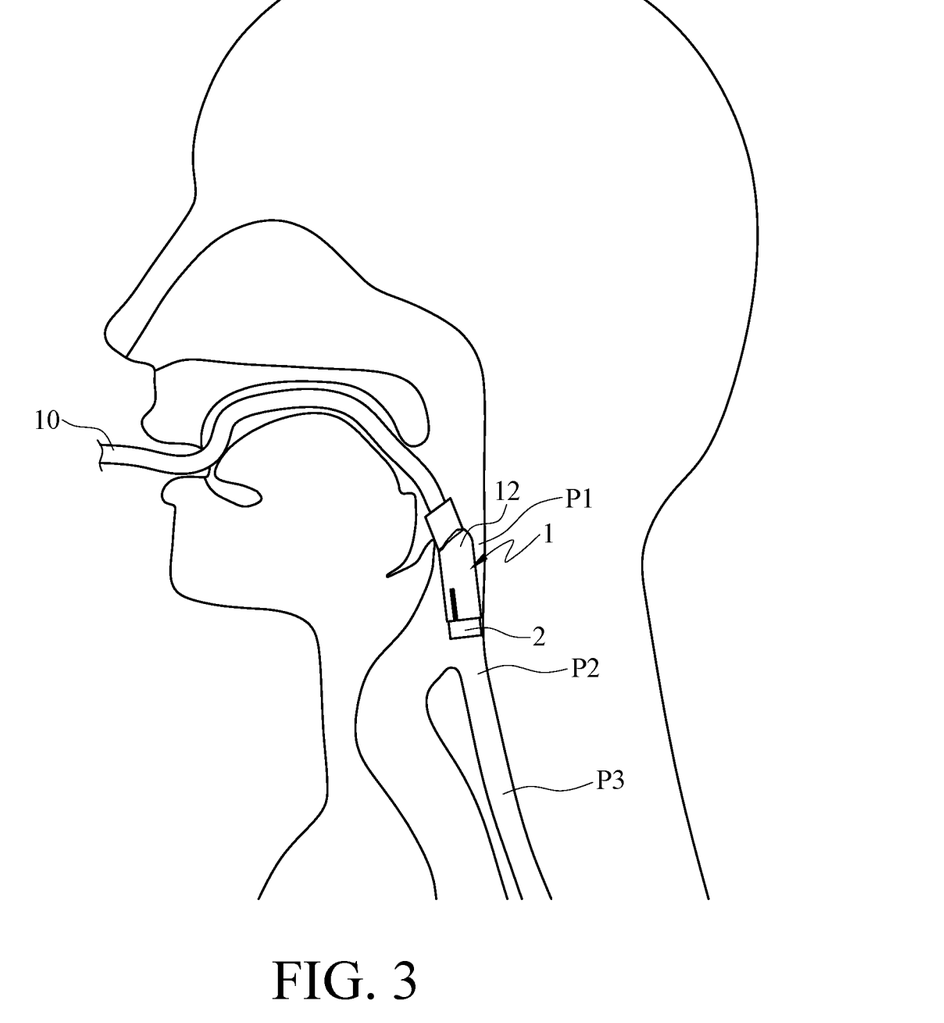
FIG. 3 is an operation diagram of the endoscopy auxiliary device according to one embodiment of the present disclosure.

For illustrating how the endoscopy auxiliary device 1 is put into a patient's body and how the endoscopy auxiliary device 1 is pulled out of the patient's body so that the capsule endoscope can be placed the patient's body, first of all, please refer to FIG. 1 and FIG. 3. FIG. 3 is an operation diagram of the endoscopy auxiliary device according to one embodiment of the present disclosure. FIG. 3 demonstrates an operation process that the endoscopy auxiliary device 1 is put into an esophagus through patient's throat. As shown in FIG. 3, the capsule endoscope 2 is clamped within the inner space 1201. During the process that a doctor pushes the endoscopy auxiliary device 1 disposed with a capsule endoscope 2 into a patient's body, the capsule endoscope 2 can be clamped tightly, and the capsule endoscope 2 is capable of passing through a throat P1 and an upper esophagus sphincter P2 for entering patient's body. It is noted that during the operation process of the endoscopy auxiliary device 1 shown in FIG. 3, only the clamper 12 of the endoscopy auxiliary device 1 and the capsule endoscope 2 clamped by the clamper 12 are put into the patient's esophagus P3 through the throat P1 and the upper esophagus sphincter P2.

In one embodiment, an intersection angle is formed between an extending direction of the pipe 120 and an extending direction of the connector 122, such as an intersection angle A shown in FIG. 2. The wire of the capsule endoscope can be more smoothly connected to external computers or displays through the intersection angle A. Moreover, since the path extending from the mouth to the esophagus P3 and passing through the throat P1 and the upper esophagus sphincter P2 is bent, the difficulty for doctors to put the endoscopy auxiliary device 1 into patients' bodies is increased. Therefore, through the intersection angle A, doctors are able to use a method matching body structures to put the capsule endoscope 2 of the endoscopy auxiliary device 1 into patients' bodies, for increasing convenience of using the endoscopy auxiliary device 1 and reducing patient's discomfort.

Figure 4:
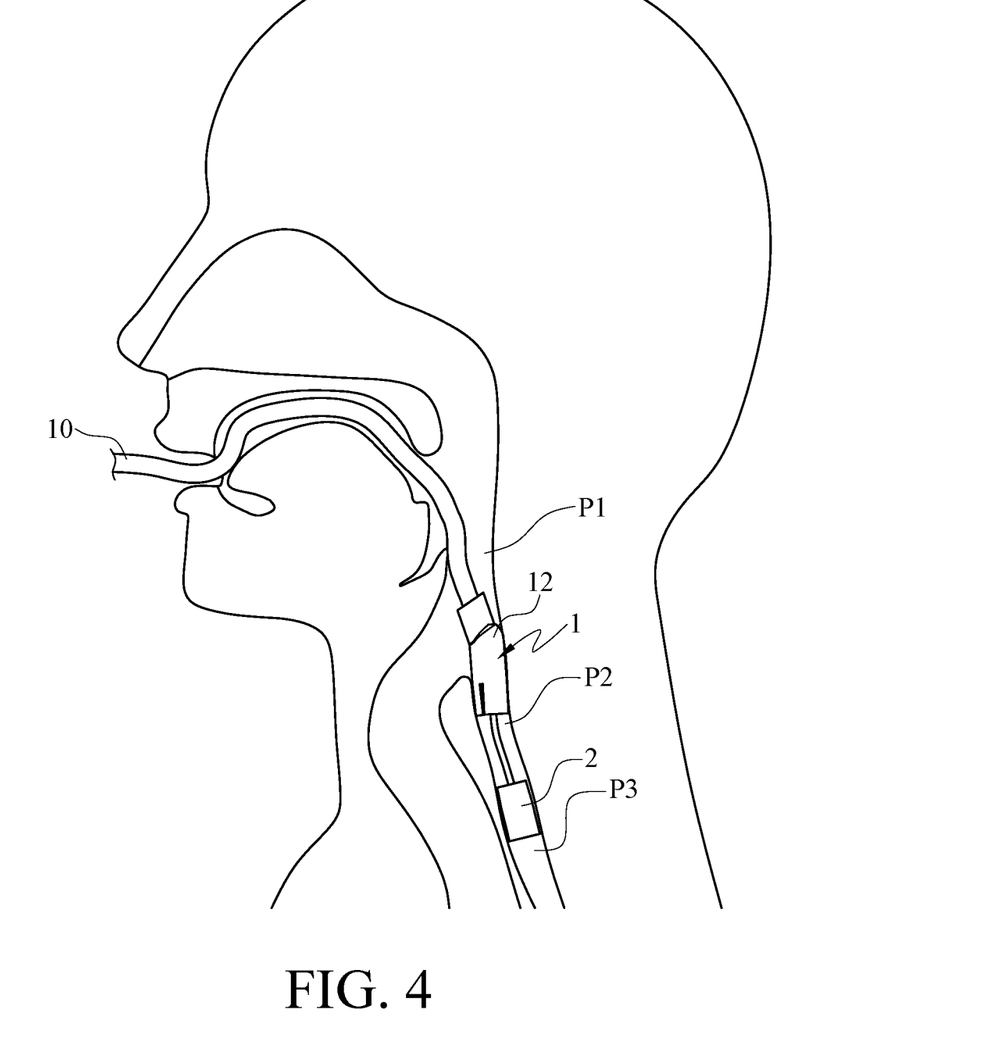
FIG. 4 is an operation diagram of the endoscopy auxiliary device according to another embodiment.

Please refer to FIG. 1 and FIG. 4. FIG. 4 is an operation diagram of the endoscopy auxiliary device according to another embodiment of the present disclosure. When the operation process in FIG. 3 is completed, FIG. 4 demonstrates the operation process that the endoscopy auxiliary device 1 is pulled out of the esophagus P3 through patient's throat P1. In general, after a doctor puts the endoscopy auxiliary device 1 disposed with the capsule endoscope 2 into the esophagus P3 through the patient's throat P1, it is necessary to pull the endoscopy auxiliary device 1 disposed with the capsule endoscope 2 out of the esophagus P3. At this time, the clamper 12, which has the second slit 1205 and the third slit 1207, are pushed by the patient's upper esophagus sphincter P2, so that the capsule endoscope 2 is pushed relatively and then dropped from the inner space 1201 of the clamper 12.

More specifically, please refer to FIG. 2 and FIG. 4, the outer surface 1209 of the clamper 12 is pushed by the upper esophagus sphincter P2 of the patient, through the second slit 1205 and the third slit 1207, the inner surface 1211 of the clamper 12 further pushes the capsule endoscope 2 placed inside the inner space 1201, so that the capsule endoscope 2 falls off and remains in the patient's esophagus P3. In a preferable embodiment, for the clamper 12, both the second distance D2 and the third distance D3 are one third of the first distance D1 and the clamper 12 is elastic. In this condition, when the endoscopy auxiliary device 1 with the capsule endoscope 2 passes through the patient's throat P1 and enters the patient's esophagus P3, the capsule endoscope 2 can be clamped effectively. When the endoscopy auxiliary device 1 is pulled out through the patient's esophagus sphincter P2, the capsule endoscope 2 can be dropped off and left inside the patient's body. However, the present disclosure is not limited to the embodiment mentioning both the second distance D2 and the third distance D3 are one third of the first distance D1.

Figure 5:
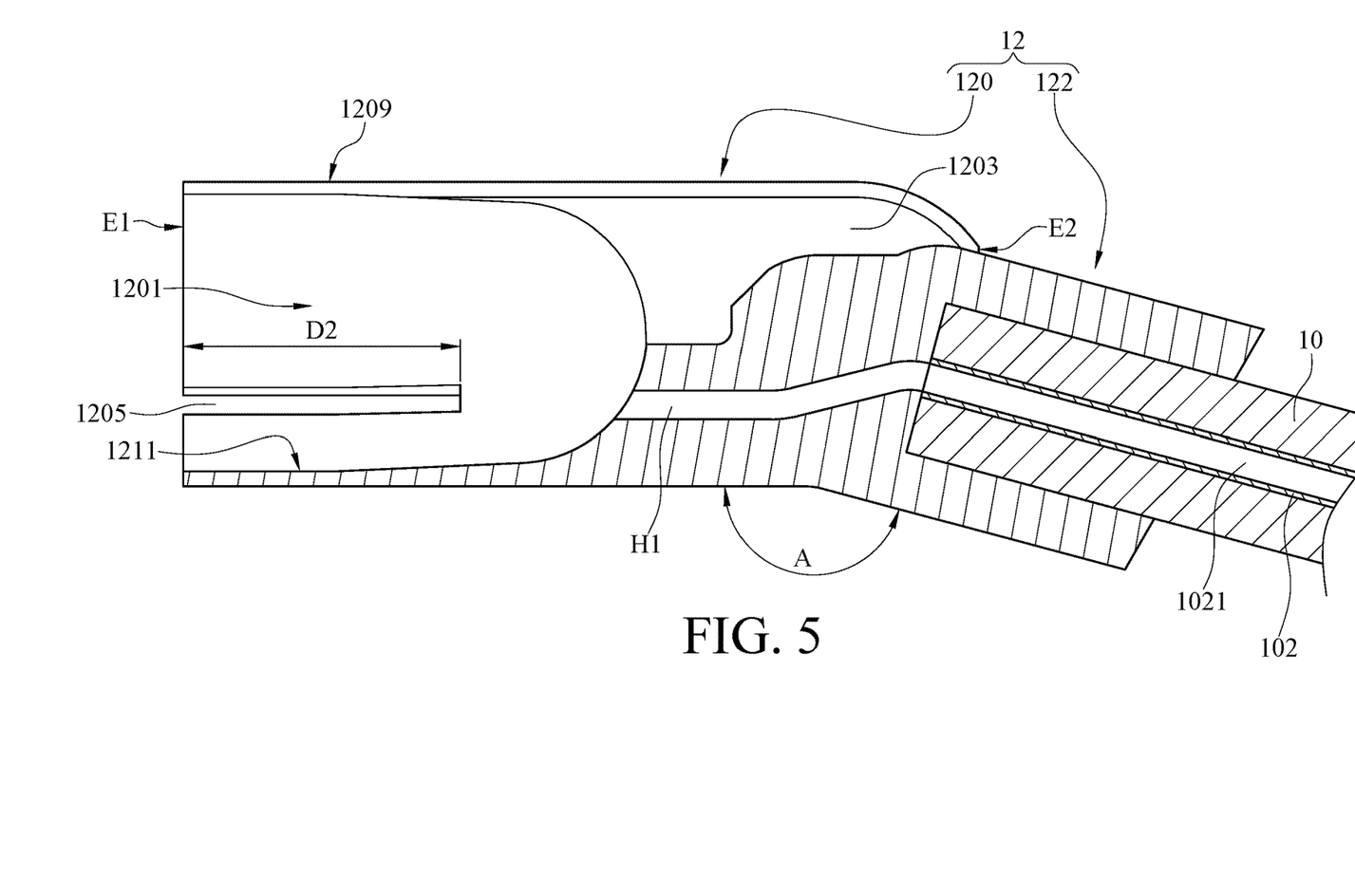
FIG. 5 is a sectional diagram of the endoscopy auxiliary device according to one embodiment of the present disclosure.

Please refer to FIG. 5, which is a sectional diagram of the endoscopy auxiliary device according to one embodiment of the present disclosure. Comparing to the embodiment of FIG. 2, in the embodiment of FIG. 5, the insertion tube 10 of the endoscopy auxiliary device 1 further has a body 102, respectively connected to the clamper 12 and either an external liquid delivering device or an external gas delivering device. Specifically, one end of the body 102 is connected to a hole H1 inside the clamper 12, and another end of the body 102 is connected to a delivering terminal (not shown in figures) of the external liquid delivering device or the external gas delivering device. In practice, the external liquid delivering device can be a liquid pump used for delivering liquid to the endoscopy auxiliary device 1 from the delivering terminal, and the external gas delivering device can be a gas pump used for delivering gas to the endoscopy auxiliary device 1 from the delivering terminal.

The body 102 has a chamber 1021 communicated with the inner space 1201 through the hole H1. When the external liquid delivering device or the external gas delivering device respectively deliver liquid or gas from the delivering terminal, liquid or gas flow into the inner space 1201 of the clamper 12 through the chamber 1021 and the hole H1, so that the capsule endoscope can be dropped off easily. For example, when doctors pull the endoscopy auxiliary device 1 carrying the capsule endoscope out of patient's body, as mentioned in the above description, the capsule endoscope in the clamper 12 would be dropped off by being pushed by the upper esophagus sphincter. At this moment, the doctor is able to further turn on the external liquid delivering device or the external gas delivering device for generating forces of liquid or gas. The forces are applied to the capsule endoscope through the chamber and the hole, so that the capsule endoscope can be more easily dropped off and left inside patient's body.

Figure 6:
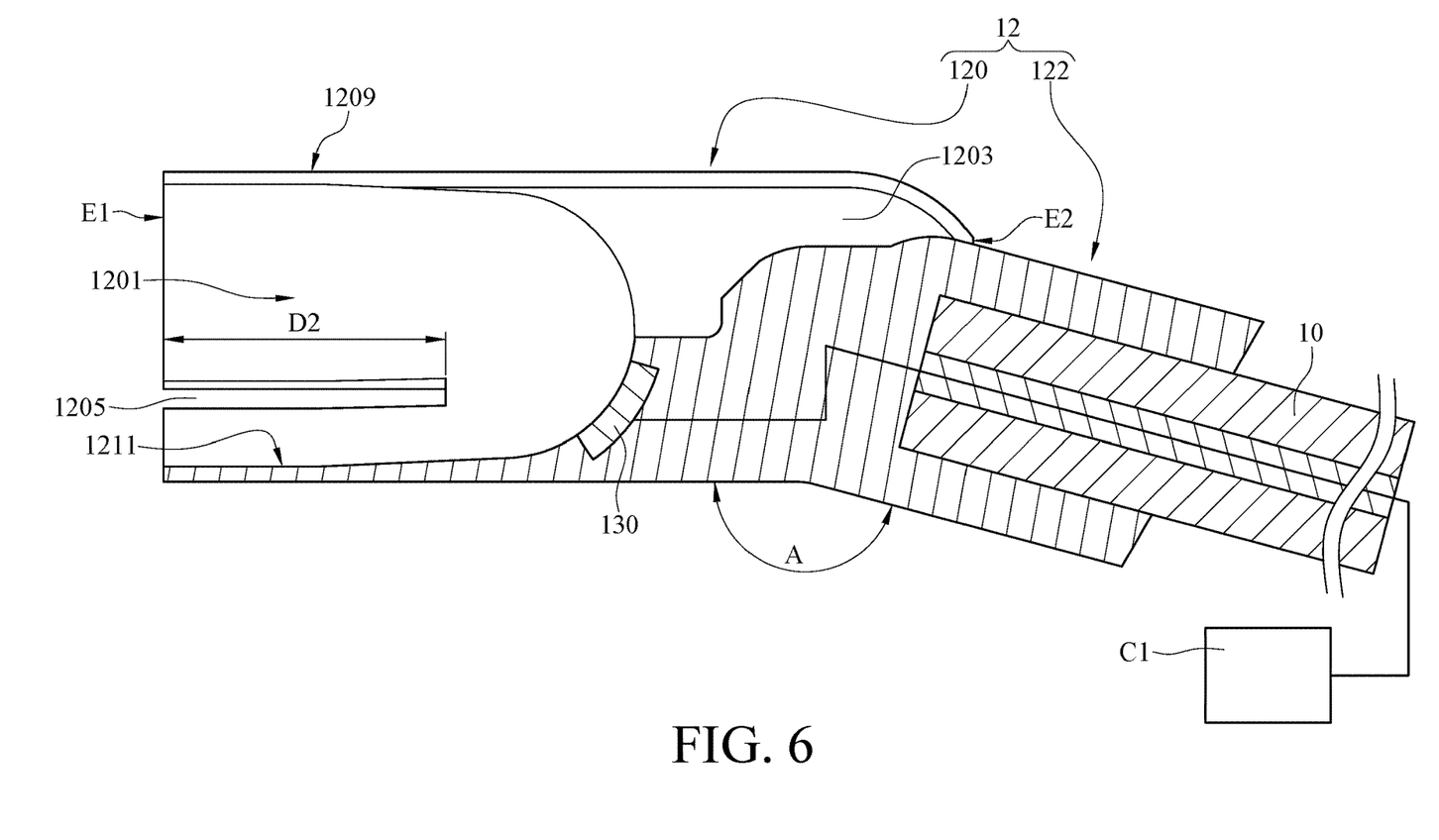
FIG. 6 is a sectional diagram of the endoscopy auxiliary device according to one embodiment of the present disclosure.

Please refer to FIG. 6, which is a sectional diagram of the endoscopy auxiliary device according to one embodiment of the present disclosure. Comparing to the embodiment of FIG. 2, in the embodiment of FIG. 6, the endoscopy auxiliary device 1 further includes a magnetic an electromagnet 130 disposed in the connector 122 and configured to receive an external current C1 for clamping or releasing the capsule endoscope. In one example, the electromagnet 130 is equipped with one or more conductive metal wires. The two ends of the one or more conductive metal wires are connected to an external power supply through the insertion tube 10. When the external power supply is turned on, the external current C1 drives the electromagnet 130 to generate a magnetic force for attracting the capsule endoscope, so that the capsule endoscope can be clamped more effectively. When the external power supply is turned off, the external current C1 disappears and then the electromagnet 130 loses the magnetic force, so that the capsule endoscope is released. It is noted that generally the capsule endoscope has one or more metal elements, so the capsule endoscope having metal elements can be attracted when the magnetic force is generated by the external current C1 received by the electromagnet 130.

In a practical example, before doctors put the endoscopy auxiliary device 1 carrying the capsule endoscope into a patient's body, the doctors are able to turn on the external power supply so that the external current flowing through metal wires drives the electromagnet to generate the magnetic force. At this time, the capsule endoscope is not only clamped by the clamper 12, but also attracted by the magnetic force of the electromagnet for increasing the clamping force for the capsule endoscope. Thereby, when the endoscopy auxiliary device 1 passes through the throat and the upper esophagus sphincter of the patient, the endoscopy auxiliary device 1 can be clamped more tightly and would not drop off before entering the esophagus. The greater the current of the electromagnet is, the greater the magnetic force is. The greater the magnetic force is, the greater the force attracting the capsule endoscope is. In practice, the location where the electromagnet is disposed is close to the capsule endoscope, so the magnetic force generated by the electromagnet is capable of attracting capsule endoscope effectively. When the doctors would like to pull the endoscopy auxiliary device 1 disposed with the capsule endoscope out of the patient's body, the doctors turn off the external power supply to stop generating the external current, so that the magnetic force of the electromagnet disappears in order to release the capsule endoscope. In this condition, the clamping force for the capsule endoscope is reduced and the capsule endoscope can be dropped of and remain in side the patient's body more easily.

In another embodiment, the capsule endoscope has a permanent magnet disposed in a fixed direction. For example, the N pole of the permanent magnet is toward the electromagnet. When a doctor puts the endoscopy auxiliary device 1 with the capsule endoscope into a patient's body, the doctor turns on the external power supply for generating a current flowing in a first direction. The current flowing in a first direction passes the electromagnet so that the electromagnet generates a magnetic force. For example, the end of the electromagnet toward the permanent magnet becomes S pole. At this time, the electromagnet and the permanent magnet in the capsule endoscope attract each other. For example, the N pole of the permanent magnet and the S pole of the electromagnet attract each other, so that the capsule endoscope can be clamped more tightly.

When the doctor pulls the endoscopy auxiliary device 1 with the capsule endoscope out of the patient's body, the doctor switches the external power supply for turning off the current flowing in the first direction and then generating another current flowing in a second direction (opposite to the first direction). The current flowing in the second direction passes the electromagnet so that the electromagnet generates magnetic force. For example, the end of the electromagnet toward the permanent magnet becomes N pole, and the electromagnet and the permanent magnet in the capsule endoscope repel each other. For example, the N pole of the permanent magnet and the N pole of the electromagnet repel each other, so that the capsule endoscope can drop off the inner space 1201 of the endoscopy auxiliary device 1. In practical operations, when the capsule endoscope drops off due to homosexual magnetic repulsion, the external power supply have to be turned off immediately, so that the electromagnet loses the magnetic force to avoid the dropped capsule endoscope being attracted back by opposite of magnetic attraction due to overturn of the capsule endoscope.

Figure 7:
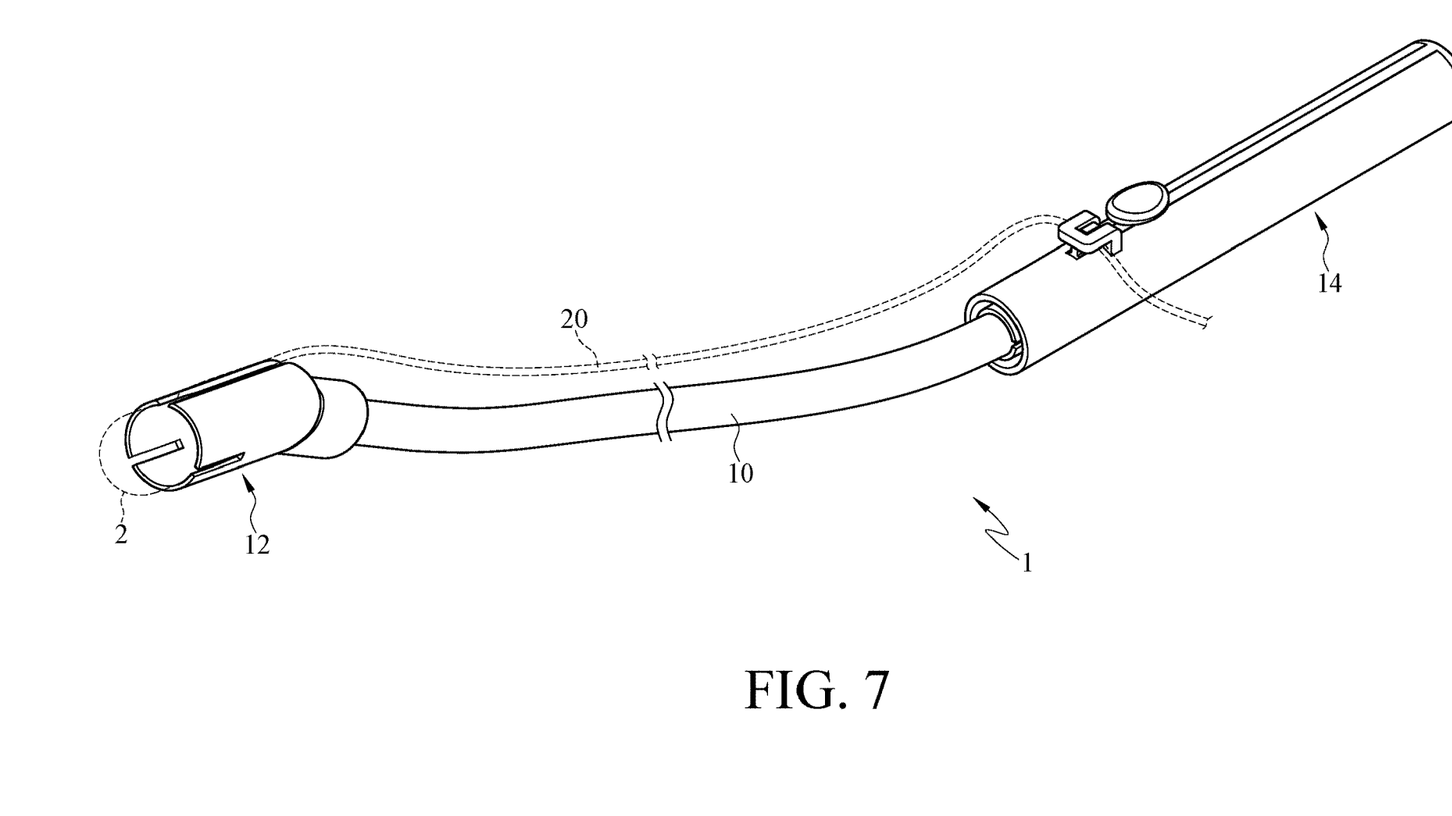
FIG. 7 is a schematic diagram of an endoscopy auxiliary device equipped with a handle according to one embodiment of the present disclosure.
Figure 8:
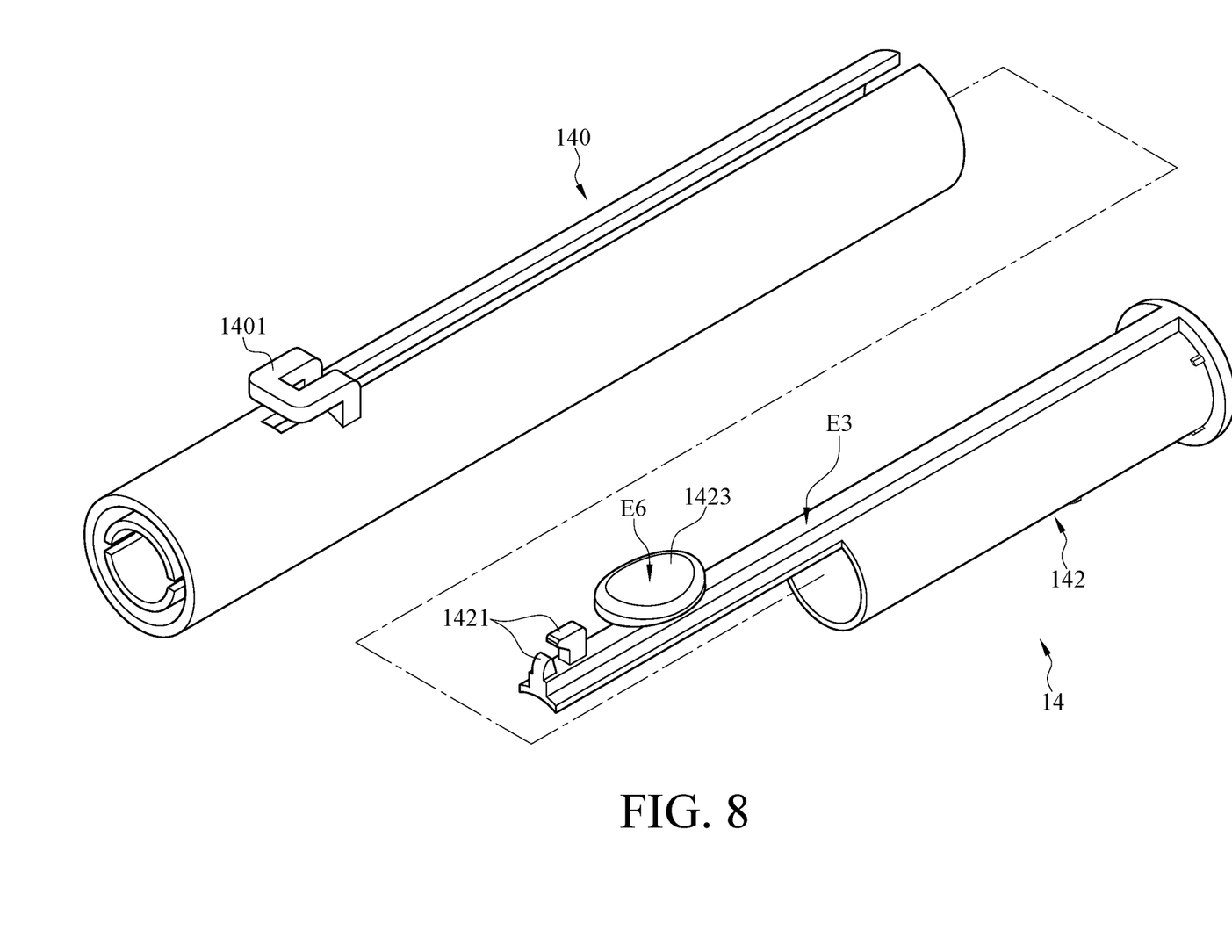
FIG. 8 is a breakdown diagram of the handle according to one embodiment of the present disclosure.
Figure 9:
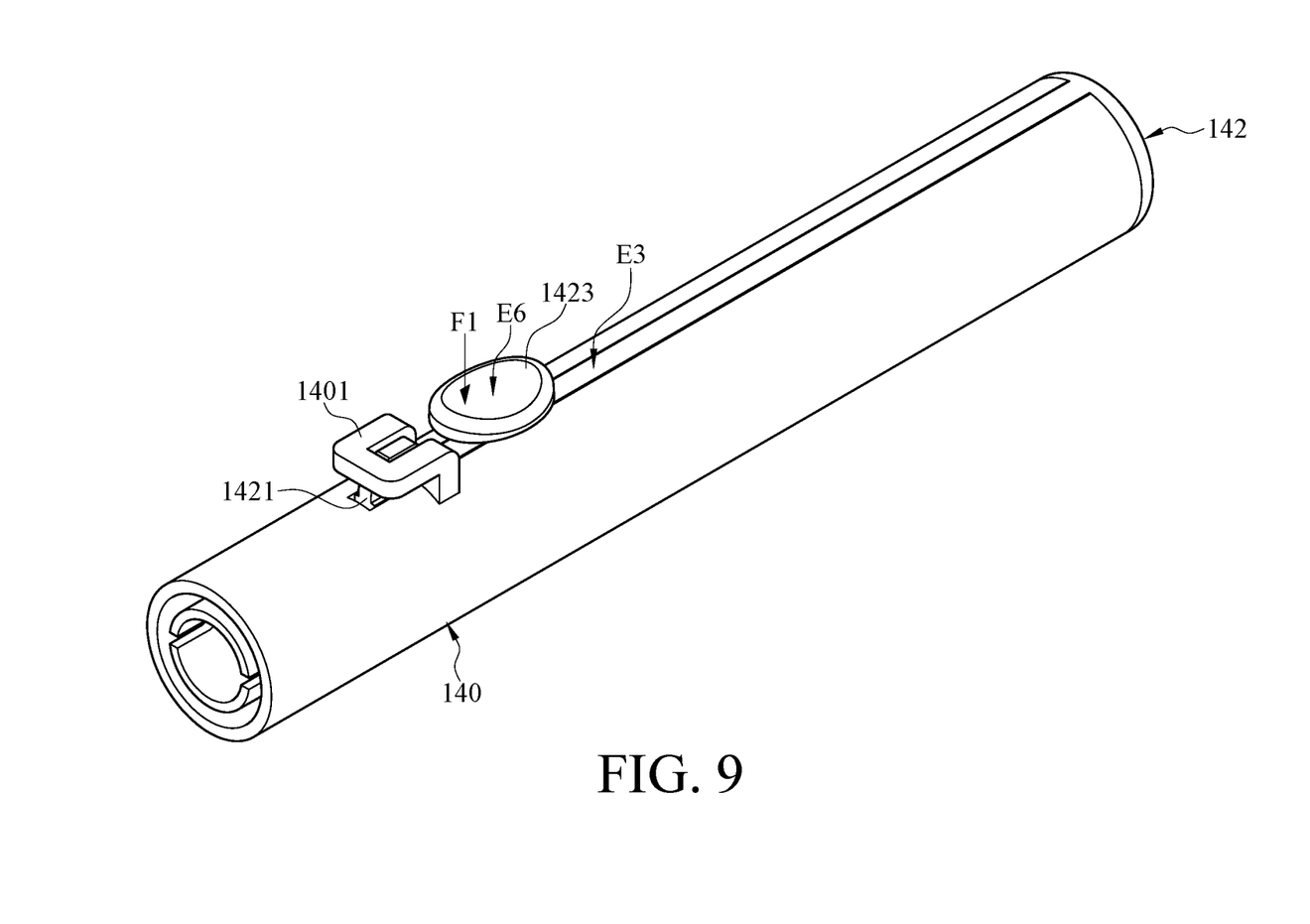
FIG. 9 is a combination diagram of the handle according to one embodiment of the present disclosure.

In some conditions, since the capsule endoscope is equipped with a wire, the inconvenience of operating the endoscopy auxiliary device is caused if the wire of the capsule endoscope is not fixed appropriately. In consideration of the conditions, please refer to FIG. 7, which is a schematic diagram of an endoscopy auxiliary device according to another embodiment of the present disclosure. As shown in FIG. 7, in addition to the insertion tube 10 and the clamper 12, the endoscopy auxiliary device 1 further includes a handle 14. The handle 14 and the clamper 12 are respectively connected to two opposite ends of the insertion tube 10. Please refer to FIG. 8 and FIG. 9. FIG. 8 is a breakdown diagram of a handle according to one embodiment of the present disclosure. FIG. 9 is a combination diagram of the handle according to one embodiment of the present disclosure. As shown in FIG. 8, the handle 14 includes a first part 140 and a second part 142. The first part 140 has one end connected to the insertion tube 10, and the first part 140 has a loop 1401. The second part 142 can be combined with the first part 140, as shown in FIG. 9. More specifically, the second part 142 can be detachably coupled with the first part 140.

Figure 10:
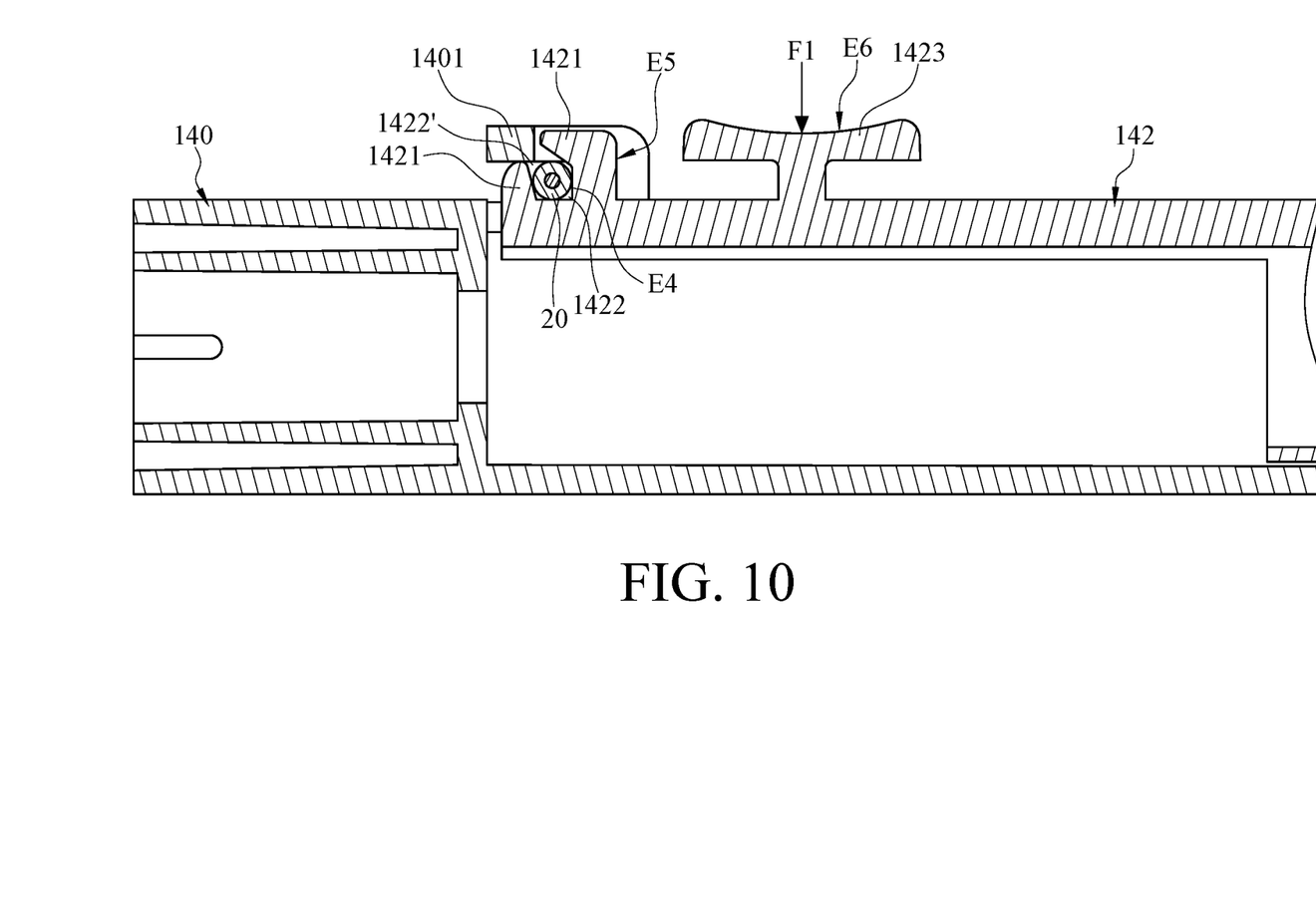
FIG. 10 is a sectional diagram of the handle according to one embodiment of the present disclosure.

Please refer to FIG. 7 to FIG. 10. FIG. 10 is a sectional diagram of the handle according to one embodiment of the present disclosure. As shown in FIG. 7 to FIG. 10, the second part 142 has a hook 1421. When the second part 142 is combined with the first part 140, the loop 1401 and the hook 1421 are able to be moved relatively. The hook 1421 has a hook slot 1422 and an opening 1422'. The hook slot 1422 is configured to accommodate a wire 20 of the capsule endoscope 2 so that the purpose of fixing the wire 20 can be achieved. It is noted that the wire 20 is presented in form of cross section in FIG. 10. The opening 1422' is communicated with an inner edge E4 of the hook slot 1422 and an outer surface E5 of the hook 1421, and the loop 1401 selectively blocks the opening 1422'. In one embodiment, the second part 142 has an actuator 1423 disposed on an outer surface E3 of the second part 142. The actuator 1423 has an operation surface E6, and the operation surface E4 faces in a force direction. The force direction is substantially the same as the direction in which the loop 1401 moves away from the opening 1422'.

A practical example is given for illustrating the operation of the handle 14. When the capsule endoscope 2 equipped with the wire 20 is disposed in the clamper 12 of the endoscopy auxiliary device 1, the wire 20 can be appropriately accommodated within the hook slot 1422. Moreover, the opening 1422' is blocked through the loop 1401 to achieve the purpose of fixing the wire 20. As a result, the operation of the endoscopy auxiliary device would not be interfered. When the capsule endoscope 2 enters into a proper location inside a patient's body, the capsule endoscope 2 is separated from the clamper 12. At this time, the operator applies an external force F1 on the operation surface E6 of the actuator 1423 as shown in FIG. 9 and FIG. 10, so that the hook 1421 moves downward relative to the loop 1401 and then the opening 1422' would not be blocked by the loop 1401. More specifically, in the embodiment, both the direction in which the loop 1401 moves away from the opening 1422' and the force direction in which the operation surface E6 faces are upward. As a result, the wire 20 can be released through the opening 1422' such that the capsule endoscope 2 is placed inside the patient's body. In this example, the actuator 1423 is similar to a button configured to be pressed by a user to drive the hook 1421 move downwards. In one embodiment, the width of the opening 1422' is slightly less than the wire diameter of a wire of the wire 20 of the capsule endoscope 2. In a practical operation, the width of the opening 1422' can be in a range of 0.85 mm to 0.95 mm, and the wire diameter of the wire 20 can be in a range of 1.0 mm to 1.1 mm. Since the hook 1421 of the second part 142 has a feature of flexibility, the hook 1421 deforms slightly when the user presses the actuator 1423 the opening 1422' such that the opening 1422' is not blocked by the loop 1401. Thereby the wire 20 is bounced out through the opening 1422' and the user would obtain a feedback, such as a vibration, of releasing the capsule endoscope 2.

Figure 11:
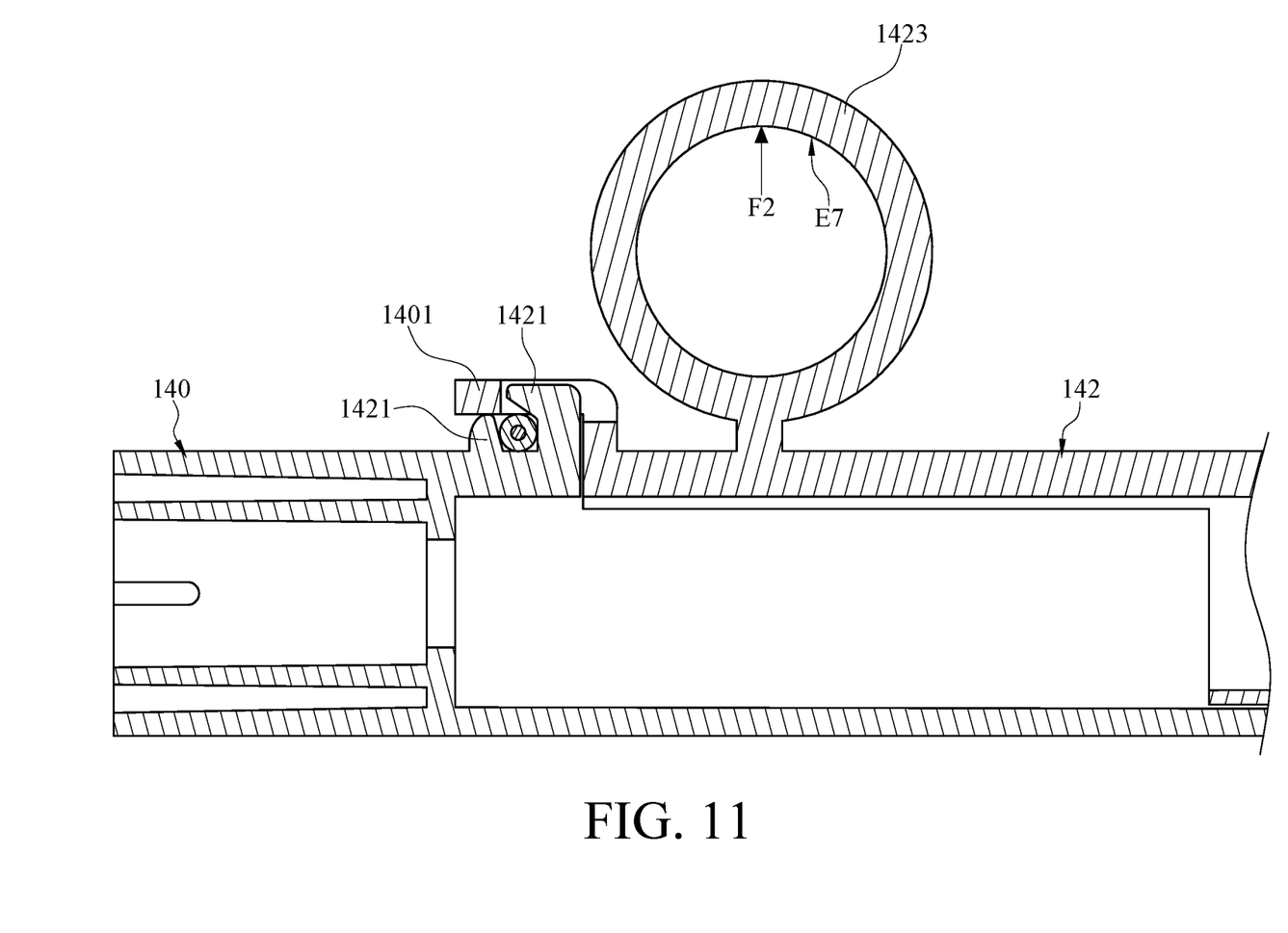
FIG. 11 is a sectional diagram of a handle according to another embodiment of the present disclosure.

Please refer to FIG. 11, which is a sectional diagram of a handle according to another embodiment of the present disclosure. Different from the embodiment of FIG. 10, in the embodiment of FIG. 11, the hook 1421 is disposed on the first part 140, and the loop 1401 is disposed on the second part 142. Similarly, the wire 20 can be accommodated within the hook slot 1422 for achieving the purposed of fixing the wire because the opening 1422' is blocked by the loop 1401. However, a difference from the embodiment of FIG. 10 lies in that, in the embodiment of FIG. 11, if the user would like to release the wire 20 through the opening 1422' of the hook 1421, it is necessary to apply an external force F2 (opposite to the external force F1 applied to the previously illustrated handle) on the operation surface E7 of the actuator 1423, such that the loop 1401 moves upwards relative to the hook 1421. As a result, the opening 1422' would not be blocked by the loop 1401, so that the wire 20 can be released through the opening 1422' and then the capsule endoscope 2 can be placed inside patients' bodies. In this example, the actuator 1423 is similar to a ring configured to be pulled by the user to drive the loop 1401 moves upwards.

Based on the above description, through the endoscope auxiliary device disclosed in the present disclosure, the capsule endoscope is clamped by the clamper such that the capsule endoscope can be put into patients' bodies through a patients' throat and upper esophagus sphincter. Moreover, when the endoscopy auxiliary device is taken out from the patient's bodies, the capsule endoscope would be pushed through the first slit, the second slit and the third slit, and then released and left in the patient's body.

What is claimed is:

1. An endoscopy auxiliary device, comprising:
    an insertion tube; and
    a clamper having a pipe and a connector, with the connector connected to the insertion tube, the pipe configured to clamp a capsule endoscope, the pipe having an inner space configured to accommodate part of the capsule endoscope, the pipe comprising:
        a first slit extending from a free end of the pipe toward a proximal end of the inner space then to a connection end of the pipe, wherein a distance between the free end and the connection end is a first distance;
        a second slit extending from the free end of the pipe for a second distance toward the connection end of the pipe; and
        a third slit extending from the free end of the pipe for a third distance toward the connection end of the pipe,
        wherein the first slit, the second slit and the third slit are separated from each other, and the first distance is greater than the second distance and the third distance.

2. The endoscopy auxiliary device according to claim 1, wherein both the second distance and the third distance are not greater than half of the first distance.

3. The endoscopy auxiliary device according to claim 2, wherein both the second distance and the third distance are one third of the first distance.

4. The endoscopy auxiliary device according to claim 1, wherein the pipe has an inner surface and an outer surface, and an extending distance of the first slit along the inner surface is less than an extending distance of the first slit along the outer surface.

5. The endoscopy auxiliary device according to claim 1, wherein the first slit is configured to accommodate a wire of the capsule endoscope.

6. The endoscopy auxiliary device according to claim 1, wherein the first slit, the second slit and the third slit are separated from each other in an equal distance.

7. The endoscopy auxiliary device according to claim 1, wherein an intersection angle is formed between an extending direction of the pipe and an extending direction of the connector.

8. The endoscopy auxiliary device according to claim 1, wherein the insertion tube has at least one flexible metal wire disposed internally.

9. The endoscopy auxiliary device according to claim 1, wherein the clamper is elastic, and the pipe is integrally connected to the connector.

10. The endoscopy auxiliary device according to claim 1, wherein the insertion tube has a body having a chamber, and the chamber is communicated with the inner space.

11. The endoscopy auxiliary device according to claim 1, further comprising:
    an electromagnet disposed in the connector and configured to selectively generate a magnetic force according to an external current for selectively attracting the capsule endoscope.

12. The endoscopy auxiliary device according to claim 1, further comprising:
    a handle, with the handle and the clamper respectively connected to two opposite ends of the insertion tube, with the handle comprising:
        a first part having one end connected to the insertion tube and having one of a loop and a hook; and
        a second part connected to the first part and having the other one of the loop and the hook;
        wherein the loop is able to be moved relatively to the hook, the hook has a hook slot and an opening, the opening extends from an inner edge defining the hook slot to an outer surface of the hook, and the loop selectively blocks the opening.

13. The endoscopy auxiliary device according to claim 12, wherein the second part has an actuator disposed on an outer surface of the second part and having an operation surface facing in a force direction, and the force direction is substantially the same as a direction in which the loop moves away from the opening.

14. The endoscopy auxiliary device according to claim 13, wherein a width of the opening is less than a wire diameter of a wire of the capsule endoscope.

* * * * *